(12) United States Patent
Frugier (10) Patent No.: US 11,285,252 B2
(45) Date of Patent: Mar. 29, 2022

(54) EXTRACORPOREAL BLOOD TREATMENT APPARATUS AND METHOD FOR CHECKING THE CONNECTION OF A SOFT BAG IN AN EXTRACORPOREAL BLOOD TREATMENT APPARATUS

(71) Applicant: GAMBRO LUNDIA AB, Lund (SE)

(72) Inventor: Alain Frugier, Chazay d'Azergues (FR)

(73) Assignee: GAMBRO LUNDIA AB, Lund (SE)

( * ) Notice: Subject to any disclaimer, the term of this patent is extended or adjusted under 35 U.S.C. 154(b) by 381 days.

(21) Appl. No.: 16/476,466

(22) PCT Filed: Dec. 29, 2017

(86) PCT No.: PCT/EP2017/084823
§ 371 (c)(1),
(2) Date: Jul. 8, 2019

(87) PCT Pub. No.: WO2018/130417
PCT Pub. Date: Jul. 19, 2018

(65) Prior Publication Data
US 2020/0054816 A1 Feb. 20, 2020

(30) Foreign Application Priority Data
Jan. 12, 2017 (EP) ..................................... 17151282

(51) Int. Cl.
*A61M 1/36* (2006.01)
*A61M 1/16* (2006.01)

(52) U.S. Cl.
CPC ............ *A61M 1/3639* (2013.01); *A61M 1/16* (2013.01); *A61M 1/369* (2013.01);
(Continued)

(58) Field of Classification Search
CPC ........ A61M 1/16; A61M 1/36; A61M 1/3639; A61M 1/369; A61M 1/3656;
(Continued)

(56) References Cited

U.S. PATENT DOCUMENTS

2014/0048460 A1* 2/2014 Paolini ................ A61M 1/3632
210/86
2016/0213829 A1* 7/2016 Klewinghaus ........ A61M 5/445
(Continued)

FOREIGN PATENT DOCUMENTS

CN 103282062 A 9/2013
CN 104220126 A 12/2014
(Continued)

OTHER PUBLICATIONS

European Search Report—Appl. No. 17151282.5-1651 dated Jul. 17, 2017—6 pages.
(Continued)

*Primary Examiner* — Philip R Wiest
(74) *Attorney, Agent, or Firm* — K&L Gates LLP (57) ABSTRACT

An extracorporeal blood treatment apparatus (1) and a method for checking the connection of a soft bag (30, 24; 33, 34) in the apparatus (1). The apparatus (1) comprises a blood treatment device (2), an extracorporeal blood circuit (3, 5) and a fluid circuit (8, 12, 15, 17, 18, 22; 41, 42, 44). A control unit (32) is configured to check the connection of a soft bag (30, 24; 33, 34) to the extracorporeal blood circuit (3, 5) or to the fluid circuit (22; 41, 42, 44) through the following procedure: sucking a medium from a connecting zone (29) through a blood pump (6) or a fluid pump (23; 37, 39) of the apparatus (1); measuring at least a pressure trend (P1, P1-P2, P2-PI, Pwdr, Pwdr-Pret, Pret-Pwdr) over time in the extracorporeal blood circuit (3, 5) or in the fluid circuit (22; 41, 42, 44) through at least a pressure sensor (25, 26); establishing from said measured pressure trend (P1, P1-P2, P2-PI, Pwdr, Pwdr-Pret, Pret-Pwdr) if the soft bag (30, 24; 33, 34) is connected to the extracorporeal blood circuit (3, 5) or to the fluid circuit (22; 41, 42, 44) at the connecting zone (29).

19 Claims, 5 Drawing Sheets

(52) U.S. Cl.
CPC . *A61M 2205/14* (2013.01); *A61M 2205/3331* (2013.01); *A61M 2205/36* (2013.01)

(58) Field of Classification Search
CPC .. A61M 2205/3331; A61M 2205/3334; A61M 2205/3337; A61M 2205/3341; A61M 2205/36
See application file for complete search history.

(56) References Cited

U.S. PATENT DOCUMENTS

2016/0220748 A1* 8/2016 Pouchoulin ......... A61M 1/3621
2016/0361485 A1* 12/2016 Tenyi ................... A61M 1/342

FOREIGN PATENT DOCUMENTS

| DE | 102013221804 | 4/2015 |
|----|--------------|--------|
| EP | 3103495 | 12/2016 |
| WO | 2015032914 | 3/2015 |
| WO | 2015036316 | 3/2015 |

OTHER PUBLICATIONS

International Search Report—Appl. No. PCT/EP2017/084823 dated Mar. 15, 2018—6 pages.
Written Opinion of the International Searching Authority—Appl. No. PCT/EP2017/084823 dated Mar. 15, 2018—9 pages.
Office Action issued by the CNPTO for corresponding Chinese Patent Application No. 2017800833534 dated Jul. 1, 2021 and received Nov. 3, 2021. English translation of same. 14 pages.

* cited by examiner

EXTRACORPOREAL BLOOD TREATMENT APPARATUS AND METHOD FOR CHECKING THE CONNECTION OF A SOFT BAG IN AN EXTRACORPOREAL BLOOD TREATMENT APPARATUS

PRIORITY CLAIM

The present application is a National Phase entry of International Application No. PCT/EP2017/084823, filed on Dec. 29, 2017, published as WO2018130417 on Jul. 19, 2018, which claims priority to European Application No. EP 17151282.5, filed on Jan. 12, 2017, the entire contents of each of which are incorporated herein by reference and relied upon.

FIELD OF THE INVENTION

The present invention relates to an extracorporeal blood treatment apparatus. The present invention relates to an extracorporeal blood treatment apparatus provided with at least a bag of the soft/flexible type configured to contain blood or other fluids to be used during blood treatment. Further, the present invention relates to an extracorporeal blood treatment apparatus provided with a blood warming device and with a warmer bag of the soft/flexible type configured to be coupled to the blood warming device. The present invention further relates to a method for checking the connection of a soft/flexible bag in an extracorporeal blood treatment apparatus.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, or to perform extracorporeal gas exchange processes, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

During extracorporeal blood treatment therapies, the patient may loose significant amount of heat due to fluid exchange by diffusion or convection, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic haemodialysis (HD), and in the case of low volume but continuous therapies like continuous renal replacement therapy (CRRT). Furthermore, the risk of hypothermia is even more problematic in case of treatments applied to low body weight patients, such as children.

Blood cooling due to fluid exchange (dialysate, infusion or both) or due to water evaporation during gas exchange processes is usually more important than heat losses to atmosphere in the complete extracorporeal blood circuit. In order to prevent hypothermia during extracorporeal blood treatment, blood warmers acting on the bloodline and capable of directly warming blood have been used.

BACKGROUND

Blood warmers are configured to heat a portion of the bloodline and to heat the blood therein. The heated portion of the blood line may be in the form of a soft bag which may be inserted in a heating seat of a warming device. The soft bag, which is usually disposable or is part of a disposable bloodline set, presents an inlet and an outlet connected to the extracorporeal blood circuit.

Document DE102013014751A1 relates to a method for controlling or regulating the pressure which, during treatment of the blood of a patient, prevails inside a heating bag of a hose system used for the treatment. It discloses to measure the pressure in the heating bag to detect excessive pressure increase in said heating bag and to stop the fluid pump to preserve the bag from damage.

Document JP2004-093230A discloses a method for testing if a soft bag-shaped medical container has any pinholes. The method comprises filling the bag with air form the liquid port and then measuring the pressure in the container.

Document US2013/0213891 discloses dialysis system and a method for detecting a filled condition of a flexible container in the dialysis system by placing a pressure sensor between the flexible container and another container.

Document DE102013221804A1 discloses a bag-warmer of a dialysis apparatus having a pressure sensor to detect the bag pressing against the sensor. The sensor serves to identify the correct position of a liquid heating bag between the two hot plates of a warmer.

A main disadvantage of most of the cited prior art documents concerns the safety of the extracorporeal blood treatment apparatuses provided with soft warmer bag.

Indeed, apart from document DE102013221804A1, none of the cited prior art documents is configured to detect the presence of the warmer bag in the warmer.

An extracorporeal blood treatment apparatus may comprise a treatment fluid circuit provided with treatment fluid line (dialysis line), for supplying a fresh treatment fluid to the treatment unit, and may comprise an evacuation fluid line leading to a receiving element, for example having a collection bag which may be of the soft/flexible type. The treatment fluid is able to receive a fresh fluid from a module, which may be a treatment fluid bag of the soft/flexible type too.

An extracorporeal blood treatment apparatus may comprise an infusion circuit comprising one or more infusion fluid lines of a replacement fluid connected to the blood circuit. The infusion circuit may be supplied by fluid coming from an infusion fluid bag which may be of the soft/flexible type too.

None of the cited prior art documents is configured to diagnose if a soft bag (by way of example, warmer bags, infusion fluid bags, treatment fluid bags, collection bags) is present in the circuit before patient treatment.

In particular, none of the cited prior art documents is configured to check the connection between the warmer bag and the blood circuit before patient treatment or before priming.

SUMMARY OF THE INVENTION

In view of the above, it is an object of the present invention to improve the safety of extracorporeal blood treatment apparatuses which blood circuit and/or other fluids circuits include a soft bag along their flow path.

In particular, it is an object of the present invention to improve the safety of extracorporeal blood treatment apparatuses provided with warming devices and soft warmer bags, optionally of disposable soft warmer bags.

It is a further object of the present invention to provide a method for detecting the connection of a soft bag for blood or other fluids in an extracorporeal blood treatment before starting patient treatment or before priming.

In particular, it is a further object of the present invention to provide a method for detecting the connection of a soft warmer bag to the blood line of an extracorporeal blood treatment before starting patient treatment or before priming. It is a further object of the present invention to provide a safe, simple and reliable method and system for checking the connection of a soft bag for blood or other fluids.

It is in particular a further object of the present invention to provide a safe, simple and reliable method and system for checking the connection of a soft warmer bag to the blood line of an extracorporeal blood treatment apparatus before starting patient treatment or before priming.

At least one of the above objects is substantially achieved by monitoring the presence of a soft/flexible bag in the circuit/s of the extracorporeal blood treatment apparatus (for instance, the blood circuit and/or the treatment circuit and/or the infusion circuit) and by checking if such soft bag is connected by measuring one or more pressures in the circuit and exploiting the ability of the soft bag to collapse (when the internal pressure decreases below the atmospheric pressure) and of acting like a one way valve. A negative pressure is installed in the part of the circuit that possibly contains the soft bag and one or more pressures in the circuit are monitored. Analysis of the measured pressure trend/s allows to determine if the soft bag is properly connected or not.

Aspects of the invention are disclosed in the following.

In accordance with a $1^{st}$ independent aspect, an extracorporeal blood treatment apparatus comprises:

a blood treatment device;

an extracorporeal blood circuit coupled to the blood treatment device;

a blood pump configured to be coupled to a pump section of the extracorporeal blood circuit;

optionally a fluid circuit operatively connected to the extracorporeal blood circuit and at least a fluid pump configured to be coupled to the fluid circuit;

wherein the extracorporeal blood circuit and/or the fluid circuit present/s a connecting zone configured to be connected to at least a soft bag respectively for blood or for a fluid;

at least a pressure sensor configured to measure at least a pressure in the extracorporeal blood circuit or in the fluid circuit;

a control unit configured to check the connection of the soft bag to the extracorporeal blood circuit or to the fluid circuit, in particular before starting patient treatment, through the following procedure:

sucking a medium from the connecting zone through the blood pump or through the fluid pump;

measuring at least a pressure trend over time in the extracorporeal blood circuit or in the fluid circuit through said at least a pressure sensor;

establishing from said measured pressure trend if the soft bag is connected to the extracorporeal blood circuit or to the fluid circuit at the connecting zone.

In accordance with a $2^{nd}$ independent aspect, an extracorporeal blood treatment apparatus comprises:

a blood treatment device;

an extracorporeal blood circuit comprising a blood withdrawal line and a blood return line coupled to the blood treatment device, wherein the extracorporeal blood circuit presents a heating zone configured to be connected to at least a soft warmer bag configured to be housed and heated in a blood warming device;

a blood pump configured to be coupled to a pump section of the blood withdrawal line;

optionally at least a fluid line connected to the extracorporeal blood circuit;

optionally at least a fluid pump configured to be coupled to said fluid line;

at least a pressure sensor configured to measure at least a pressure in the extracorporeal blood circuit;

a control unit configured to check the connection of the soft warmer bag to the extracorporeal blood circuit, in particular before starting patient treatment, through the following procedure:

sucking a fluid from the heating zone through the blood pump or through the fluid pump or both of them;

measuring at least a pressure trend over time in the extracorporeal blood circuit through said at least a pressure sensor;

establishing from said measured pressure trend if the soft warmer bag is connected to the extracorporeal blood circuit at the heating zone.

In accordance with a $3^{rd}$ independent aspect, a method for checking the connection of a soft bag in an extracorporeal blood treatment apparatus, comprises:

sucking a medium from a connecting zone of an extracorporeal blood circuit or of a fluid circuit, wherein the connecting zone is configured to be connected to at least a soft bag respectively for blood or for a fluid, wherein sucking is performed through a blood pump of the extracorporeal blood circuit or through a fluid pump of the fluid circuit;

measuring at least a pressure trend over time in the extracorporeal blood circuit or in the fluid circuit;

establishing from said measured pressure trend if the soft bag is connected to the extracorporeal blood circuit or to the fluid circuit at the connecting zone.

In accordance with a $4^{th}$ independent aspect, a method for checking the connection of a soft warmer bag in an extracorporeal blood treatment apparatus, before starting patient treatment, comprises:

sucking a medium from a heating zone of an extracorporeal blood circuit (3, 5), wherein the heating zone is configured to be connected to at least a soft warmer bag configured to be housed and heated in a blood warming device, wherein sucking is performed through a blood pump of the extracorporeal blood circuit or a fluid pump of a fluid line connected to a treatment device or to the extracorporeal blood circuit or both of them;

measuring at least a pressure trend over time in the extracorporeal blood circuit;

establishing from said measured pressure trend if the soft warmer bag is connected to the extracorporeal blood circuit at the heating zone.

The way to detect the bag connection is identified by using the bag propensity to collapse. If the bag is connected, sucking the medium implies that the soft bag starts to collapse until it works like a closed valve and sucking is prevented or almost prevented. It is not possible for the pump to suck the medium from the bag which collapses as soon as its internal pressure becomes lower than atmospheric pressure. If the bag is not connected, sucking the medium does not imply the soft bag to collapse. The pressure trend over time in these two situations is different and allows to establish if the bag is connected or not. In particular, the trend of a measured pressure (or pressures difference or integrated values of said pressure or of said pressure difference) with the soft bag installed is different from a pressure trend of the same pressure (or pressures difference or integrated values of said pressure or of said pressure difference) when the soft bag is not present.

In a $5^{th}$ aspect according to the previous aspects 1 or 3, a first line of the blood circuit or of the fluid circuit departs from the connecting zone and said at least a pressure sensor is a first pressure sensor placed between the connecting zone and the blood pump or the fluid pump configured to be coupled to said first line; wherein measuring at least a pressure trend over time comprises: measuring a first pressure in the first line.

In a $6^{th}$ according to the previous aspect, a second line of the blood circuit or of the fluid circuit departs from the connecting zone and wherein a second pressure sensor is placed between the connecting zone and a clamp placed in the second line; wherein measuring at least a pressure trend over time comprises: measuring a second pressure in the second line and calculating a pressure difference between the first pressure and the second pressure.

In a $7^{th}$ aspect according to the previous aspect, the first line is an inlet line into the connecting zone and the second line is an outlet line from the connecting zone or vice-versa.

In a $8^{th}$ aspect according to the previous aspects 5, 6 or 7, the first line is a blood withdrawal line of the extracorporeal blood circuit; the first pressure is a withdrawal pressure; wherein the connecting zone is a heating zone and the soft bag is a soft warmer bag; wherein the heating zone is configured to be connected to the soft warmer bag configured to be housed and heated in a blood warming device.

In a $9^{th}$ aspect according to the previous aspect, the second line is a blood return line of the extracorporeal blood circuit; wherein the second pressure is a return pressure.

In a $10^{th}$ aspect according to any of the previous aspects 1, 3, 5-9, the fluid circuit is a treatment fluid circuit or an infusion circuit; the first line is a fluid line and the soft bag is a dispenser bag for a fluid to be dispensed or a collection bag for a waste fluid to be collected.

In a $11^{th}$ aspect according to the previous aspects 2, 4 or 10, said at least a fluid line comprises a treatment fluid line connected to the blood treatment device.

In a $12^{th}$ aspect according to the previous aspect, said at least a fluid pump comprises a treatment fluid pump configured to be coupled to the treatment fluid line.

In a $13^{th}$ aspect according to one of the previous aspects 2, 4, 10-12, said at least a fluid line comprises an evacuation fluid line connected to the treatment device.

In a $14^{th}$ aspect according to the previous aspect, said at least a fluid pump comprises an evacuation fluid pump configured to be coupled to the evacuation fluid line.

In a $15^{th}$ aspect according to one of the previous aspects 2, 4, 10-14, said at least a fluid line comprises at least an infusion fluid line connected to the extracorporeal blood circuit.

In a $16^{th}$ aspect according to the previous aspect, said at least a fluid pump comprises at least an infusion fluid pump configured to be coupled to the infusion fluid line.

In a $17^{th}$ aspect according to the previous aspects 15 or 16, the infusion fluid line is at least one of: a pre-infusion line, a pre-pump infusion line, a post infusion line.

In a $18^{th}$ aspect according to one of the previous aspects 2, 9-17, the heating zone is placed in the blood return line.

In a $19^{th}$ aspect according to one of the previous aspects 2, 8-18, said at least a pressure sensor comprises a withdrawal pressure sensor placed in the blood withdrawal line.

In a $20^{th}$ aspect according to the previous aspect, the withdrawal pressure sensor is a filter pressure sensor placed between the blood pump and the blood treatment device, optionally just upstream the blood treatment device.

In a $21^{st}$ aspect according to one of the previous aspects 2, 9-20, said at least a pressure sensor comprises a return pressure sensor placed in the blood return line.

In a $22^{nd}$ aspect according to the previous aspect, the heating zone is placed between the blood treatment device and the return pressure sensor.

In a $23^{rd}$ aspect according to one of the previous aspects 2, 9-22, the apparatus comprises a return clamp placed on the blood return line.

In a $24^{th}$ aspect according to the previous aspect, the return pressure sensor is placed between the heating zone and the return clamp.

In a $25^{th}$ aspect according to one of the previous aspects 13 or 14, said at least a pressure sensor is an evacuation pressure sensor placed in the evacuation fluid line.

In a $26^{th}$ aspect according to the previous aspect, the evacuation pressure sensor is placed between the blood treatment device and the evacuation fluid pump.

In a $27^{th}$ aspect according to aspect 12, a first pinch valve is placed on the treatment fluid line, between the blood treatment device and the treatment fluid pump, optionally the first pinch valve is placed at a branching point of the treatment fluid line and of a post-infusion branch.

In a $28^{th}$ aspect according to the previous aspect, when sucking the medium from the heating zone, the first pinch valve is in a post position to deliver the fluid as a post dilution fluid.

In a $29^{th}$ aspect according to previous aspect 27, when sucking the medium from the heating zone, the first pinch valve is in a neutral position, in which said pinch valve does not pinch any tube.

In a $30^{th}$ aspect according to aspect 16 or 17, a second pinch valve is placed on the infusion fluid line, between the extracorporeal blood circuit and the infusion fluid pump, optionally the second pinch valve is placed at a branching point of a pre-infusion line and a post-infusion line.

In a $31^{st}$ aspect according to the previous aspect, when sucking the medium from the heating zone, the second pinch valve is in post position to deliver the fluid as a post dilution fluid.

In a $32^{nd}$ aspect according to the previous aspects, the medium is air.

In a $33^{rd}$ aspect according to the previous aspect when referring to aspects 2, 4 or 8-32, when sucking the medium from the heating zone, the extracorporeal blood circuit is empty of blood or of priming fluid.

In a 34th aspect according to the previous aspects from 1 to 31, the medium is priming fluid. Using priming fluid instead of room air prevents from introducing risk of infection.

In a 35th aspect according to the previous aspects 2, 4 or 8-33, when sucking a medium from the heating zone, the extracorporeal blood circuit is in fluid communication with the external environment.

In a 36th aspect according to the previous aspects 2, 4 or 8-34, when sucking a medium from the heating zone, the extracorporeal blood circuit is sealed form the external environment.

In a 37th aspect according to the previous aspects, checking the connection of the soft bag to the extracorporeal blood circuit or to the fluid circuit is performed before priming.

In a 38th aspect according to the previous aspects, checking the connection of the soft bag to the extracorporeal blood circuit or to the fluid circuit is performed after priming.

In a 39th aspect according to the previous aspects 2, 4, 8-38, sucking a medium from a heating zone comprises: moving said fluid in an opposite direction with respect to the blood flow direction during patient treatment.

In a 40th aspect according to the previous aspects 2, 4, 8-39, sucking a medium from a heating zone comprises: running the blood pump backwards with respect to blood withdrawal from patient during treatment.

In a 41st aspect according to the previous aspects 2, 4, 8-40, sucking a medium from a heating zone comprises: running the blood pump with a flow rate comprised between about 10 and about 500 ml/min, optionally between 50 and 150 ml/min.

In a 42nd aspect according to the previous aspects 2, 4, 8-41, sucking a medium from a heating zone comprises: running the fluid pump backwards with respect to patient treatment.

In a 43rd aspect according to the previous aspects 2, 4, 8-42, sucking a medium from a heating zone comprises: running the fluid pump with a flow rate comprised between about 10 and about 500 ml/min, optionally between 50 and 150 ml/min.

In a 44th aspect according to the previous aspects 2, 8-43, the heating zone is placed in the blood return line and said at least a fluid line is placed upstream the heating zone with respect to the blood flow during patient treatment; wherein sucking a medium from a heating zone comprises: running the blood pump backwards with respect to blood withdrawal from patient during treatment or running the fluid pump backwards with respect to patient treatment or running backwards both of them.

In a 45th aspect according to the previous aspects 23 or 24, the return clamp is kept open when sucking a medium from a heating zone.

In a 46th aspect according to the previous aspects 23 or 24, when sucking the fluid from the heating zone, the return clamp is closed.

In a 47th aspect according to the previous aspects 2 or 8-46, measuring at least a pressure trend over time comprises: measuring a withdrawal pressure in the blood withdrawal line.

In a 48th aspect according to the previous aspect, the withdrawal pressure is measured between the blood pump and the blood treatment device, optionally just upstream (with respect to blood flow direction during patient treatment) the blood treatment device.

In a 49th aspect according to the previous aspects 2 or 9-48, measuring at least a pressure trend over time comprises: measuring a return pressure in the blood return line.

In a 50th aspect according to the previous aspect, the return pressure is measured downstream (with respect to blood flow direction during patient treatment) the heating zone.

In a 51st aspect according to the previous aspects 49 or 50 when they refer to aspects 47 or 48, measuring at least a pressure trend over time comprises: calculating a pressure difference between the withdrawal pressure and the return pressure.

In a 52nd aspect according to the previous aspect, sucking a medium from a heating zone comprises: running the blood pump backwards with respect to blood withdrawal from patient during treatment, wherein the measured pressure trend is obtained by subtracting the return pressure from the withdrawal pressure.

In a 53rd aspect according to aspect 50, sucking a medium from a heating zone comprises: running the fluid pump backwards with respect to patient treatment, wherein the measured pressure trend is obtained by subtracting the withdrawal pressure from the return pressure.

In a 54th aspect according to any of the previous aspects 49 to 53 when they refer to aspects 47 or 48, measuring at least a pressure trend over time comprises: calculating an integrated value of a pressure difference between the withdrawal pressure and the return pressure.

In a 55th aspect according to the previous aspects, establishing from said measured pressure trend if the warmer bag is connected comprises: determining if the measured pressure trend changes (decreases or increases) or not.

In a 56th aspect according to the previous aspect, determining if the measured pressure trend changes or not is performed during sucking or after sucking or during and after sucking.

In a 57th aspect according to the previous aspects 55 or 56, determining if the measured pressure trend changes or not is performed during a time frame.

In a 58th aspect according to the previous aspect, said time frame is comprised between about 5 s and about 30 s, optionally between about 10 s and about 20 s.

In a 59th aspect according to one of the previous aspects form 55 to 58, if the measured pressure trend decreases the soft bag is connected and if the measured pressure trend remains substantially steady or increases the soft bag is not connected.

In a 60th aspect according to one of the previous aspects form 55 to 58, if the measured pressure trend remains substantially steady or increases the soft bag is connected and if the measured pressure trend decreases the soft bag is not connected.

In a 61st aspect according to the previous aspects, establishing from said measured pressure trend if the soft bag is connected comprises: comparing said at least a measured pressure trend with at least a predetermined pressure trend.

In a 62nd aspect according to the previous aspect, the predetermined pressure trend is a constant value (pressure threshold for soft bag presence), optionally equal to zero, optionally lower than zero.

In a 63rd aspect according to the previous aspects 2, 9-62, the method and the procedure comprises:
 i. setting values of a withdrawal pressure in the blood withdrawal line and of a return pressure in the blood return line while the blood pump and the fluid pump are stopped;
 ii. sucking the medium from the heating zone through the blood pump or through the fluid pump while measuring the withdrawal pressure and the return pressure;

iii. stopping the blood pump or the fluid pump and keep on measuring the withdrawal pressure and the return pressure.

In a 64th aspect according to the previous aspects, the control unit triggers a warning if the soft bag is not properly connected.

In a 65th aspect according to the previous aspects, the control unit compares the pressure trend over time with a reference, e.g. a pre-stored reference, before establishing from said measured pressure trend if the soft bag is connected. The pre-stored reference is in particular empirically determined.

In a 66th aspect according to any previous aspects, the soft bag is empty or substantially empty from liquids.

In a 67th aspect according to any previous aspects, the soft bag contains air, in particular contains substantially exclusively air.

In a 68th aspect according to any previous aspects, the medium is a gas, in particular air.

DESCRIPTION OF THE DRAWINGS

The following drawings relating to aspects of the invention are provided by way of non-limiting example.

DETAILED DESCRIPTION

Figure 1:
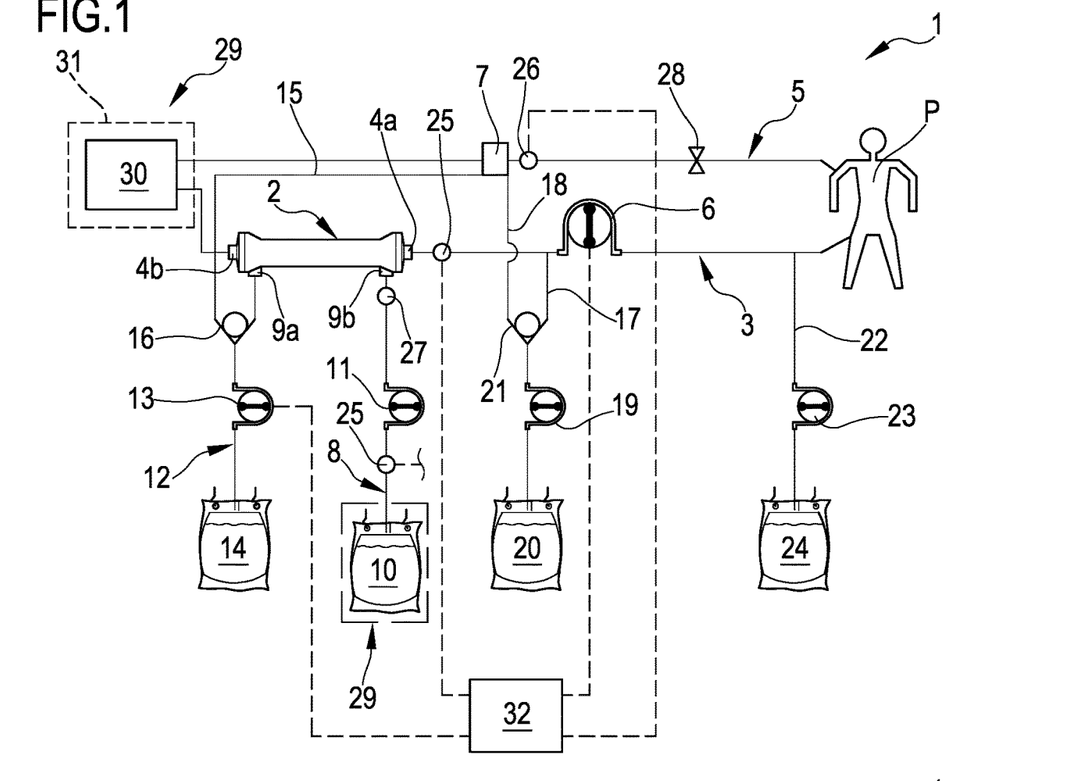
FIG. 1 shows a schematic representation of an extracorporeal blood treatment apparatus provided with a soft warmer bag and able to detect the presence of the soft warmer bag according to the method and procedure of the present invention.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter, a membrane oxygenator or other unit suitable for processing the blood taken from a patient P. The blood treatment device 2 has a first compartment or blood chamber and a second compartment or fluid chamber separated from one another by a semipermeable membrane, not shown. A blood withdrawal line 3 is connected to an inlet port 4a of the blood chamber and is configured, in an operative condition of connection to the patient P, to remove blood from a vascular access device inserted, for example in a catheter on the patient P. A blood return line 5 connected to an outlet port 4b of the blood chamber is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on.

As shown in FIG. 1, the apparatus 1 comprises at least a first actuator, in the present example a blood pump 6, which operates at the blood withdrawal line 3, to cause movement of the blood removed from the patient P from a first end of the withdrawal line 3 connected to the patient P to the blood chamber. The blood pump 6 is, for example, a peristaltic pump, as shown in FIG. 1, which acts on a respective pump section of the withdrawal line 3. When rotated, e.g., counter-clockwise, the blood pump 6 causes a flow of blood along the blood withdrawal line 3 towards the blood chamber (see the arrows in FIG. 1 indicative of the blood flow along the blood withdrawal line 3).

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 3 connected to the patient P towards the blood chamber and then from the blood chamber towards a second end of the blood return line 5 connected to the vascular access of the patient P.

The apparatus 1 further comprises an air trap 7 operating on the blood return line 5 (the air trap 7 is a venous deareation chamber). The air trap 7 is placed online in the blood return line 5. A first section of the blood return line 5 puts in fluid communication the outlet port 4b of the blood chamber with the air trap 7 and a second section of the blood return line 5 puts in fluid communication the air trap 7 with the patient P. The blood coming from the blood chamber of the treatment device 2 enters and exits the air trap 7 before reaching the patient P.

The blood withdrawal line 3, the blood return line 5 and the air trap 7 are part of an extracorporeal blood circuit of the apparatus 1.

The apparatus 1 further comprises one evacuation fluid line 8 connected with an outlet port 9b of the fluid chamber such as to receive at least a filtered fluid through the semipermeable membrane. The evacuation fluid line 8 receives the waste fluid coming from the fluid chamber of the treatment device 2, for example, comprising used dialysis liquid or liquid ultra-filtered through the membrane. The evacuation fluid line 8 leads to a receiving element, for example having a collection bag 10 or a drainage pipe, for the waste fluid. An evacuation fluid pump 11 may operate on the evacuation fluid line 8.

In the example of FIG. 1, a treatment fluid circuit is also present. The treatment fluid circuit comprises a treatment fluid line 12 (dialysis line), for supplying a fresh treatment fluid to an inlet port 9a of the fluid chamber. The treatment fluid line 12 is equipped with a treatment fluid pump 13 (dialysis pump) and is able to receive a fresh fluid from a module, for example a treatment fluid bag 14 or on-line preparation section of treatment fluid, and to send such a fluid to the inlet port 9a of the fluid chamber. The treatment fluid circuit may comprise a post-infusion branch 15 departing from a branching point of the treatment fluid line 12 located between the blood treatment device 2 and the treatment fluid pump 13. The post-infusion branch 15 is connected to the air trap 7 or to the return line 5. A first pinch valve 16 is placed at the branching point and it is configured to be set in a first, second and third position to selectively pinch the tubes of the treatment fluid line 12 and of the post-infusion branch 15. The first pinch valve 16 allows the fluid contained in the bag 14 to be delivered either in the fluid chamber of the blood treatment device 2 (first—dial position) or in the air trap 7 as a post dilution fluid (second—post position). The first pinch valve 16 may be set in a third (neutral) position which does not pinch any tube. In this third position, the air trap 7 is in fluid communication with the fluid chamber of the blood treatment device 2. The evacuation fluid line 8, the treatment fluid line 12, the post-infusion branch 15 and the fluid chamber are part of a treatment fluid circuit.

The apparatus 1 comprises an infusion circuit comprising one or more infusion fluid lines 17, 18 of a replacement fluid. In the apparatus of FIG. 1, a pre-infusion line 17 is connected to the blood withdrawal line 3, between the blood pump 6 and the blood treatment device 2, and a post-infusion line 18 is connected to the air trap 7 of the blood return line 5. An infusion fluid pump 19 equips the infusion circuit. The infusion circuit of the apparatus shown in FIG. 1 is supplied by fluid coming from an infusion fluid bag 20 or may be supplied directly by infusion fluid prepared on-line.

A second pinch valve 21 is placed at a branching point of the pre- and post-infusion lines 17, 18 and it is configured to be set in a first, second and third position to selectively pinch the tubes of the pre- and post-infusion lines 17, 18.

The second pinch valve 21 allows the fluid contained in the infusion fluid bag 20 to be delivered either between the blood pump 6 outlet and the inlet port 4a of blood chamber as a pre dilution fluid (first—pre position) or in the air trap 7 as a post dilution fluid (second—post position).

The second pinch valve 21 may be set in a third (neutral) position which does not pinch any tube. In this third position, the air trap 7 is in fluid communication with a section of the blood withdrawal line 3 located between the blood pump 6 and the inlet port 4a.

The apparatus 1 shown in FIG. 1 comprises also a pre-pump infusion line 22 connected to the blood withdrawal line 3 upstream of the blood pump 6. An auxiliary infusion fluid pump 23 equips the pre-pump infusion line 22. The pre-pump infusion line 22 of the apparatus shown in FIG. 1 is supplied by fluid coming from an auxiliary infusion fluid bag 24 or may be supplied directly by infusion fluid prepared on-line.

The above mentioned treatment fluid line 12 with the post-infusion branch 15, the evacuation fluid line 8, the pre-infusion and post-infusion lines 17,18 and the pre-pump infusion line 22 are part of a fluid circuit operatively connected to the extracorporeal blood circuit 3, 5.

A first pressure sensor or withdrawal pressure sensor 25 is placed in the blood withdrawal line 3 close to the inlet port 4a of blood chamber of the blood treatment device 2. The withdrawal pressure sensor 25 is a filter pressure sensor placed between the blood pump 6 and the blood treatment device 2. The first pressure sensor or withdrawal pressure sensor 25 is configured to measure e first pressure "P1" which in this case is a withdrawal pressure "Pwdr". A second pressure sensor or return pressure sensor 26 is placed in the blood return line 5 and it is active in the air trap 7 or downstream of said air trap 7. The second pressure sensor or return pressure sensor 26 is configured to measure e second pressure "P2" which in this case is a return pressure "Pret". An evacuation pressure sensor 27 is placed in the evacuation fluid line 8 between the blood treatment apparatus 2 and the evacuation fluid pump 11. A return clamp 28 is placed on the blood return line 5 downstream of the return pressure sensor 26.

The blood return line 5 of the apparatus 1 presents a heating zone 29 configured to be connected to a disposable soft warmer bag 30. The heating zone 29 is placed between the blood treatment device 2 and the air trap 7, such that the return pressure sensor 26 is placed between the heating zone 29 and the return clamp 28.

The soft warmer bag 30 is configured to be housed and heated in a blood warming device 31, only schematically shown in FIG. 1.

The soft warmer bag 30 may be a substantially flat bag insertable in a heating seat provided in the heating unit of the warming device 31. The soft warmer bag 30 is made of a thermally conductive plastic material and presents an inlet and an outlet connected to the blood return line 5.

By way of example, the soft warmer bag 30 may be made of two sheets of thermally conductive plastic film material bonded together in a pattern which creates a fluid channel between the sheets. The fluid channel may present a serpentine pattern. The material may be polyvinyl chloride (PVC) or polyurethane. With the term "soft" referred to the warmer bag 30 it is meant that the bag 30 may be deformed by the differential pressure acting inside and outside the bag 30 itself, such that if the pressure inside the bag is lower than the outside/atmospheric pressure, the bag may collapse.

The apparatus 1 comprises a control unit 32 schematically represented in FIG. 1. The control unit may comprise a digital processor (CPU) and memory (or memories), an analog circuit, or a combination thereof. Said control unit 32 may be the control unit which is configured to control the apparatus during patient blood treatment. The control unit 32 is connected at least to the blood pump 6 and the treatment fluid pump 13, to the withdrawal pressure sensor 25 and to return pressure sensor 26. Connections between the control unit and other units are generally illustrated (but not necessarily always) in the figures by dotted lines.

Prior to patient treatment, said control unit is configured to check the connection of the soft warmer bag 30 to the extracorporeal blood circuit 3, 5 according to the procedure and to the method of the invention.

To this aim, after the extracorporeal blood circuit 3, 5 with the blood treatment device 2 has been loaded and while the circuit is empty (or full of air), the blood pump 6 and/or the treatment fluid pump 13 is/are enabled to run backwards, with respect to the running conditions during patient treatment, for a time frame "Δt". In this way, a fluid (air) is sucked from the heating zone in a direction opposite to the blood/fluid flow direction during patient treatment. During sucking and optionally after, signals from the withdrawal pressure sensor 25 and from the return pressure sensor 26 are detected and processed by the control unit 32, in order to measure at least a pressure trend over time in the extracorporeal blood circuit 3, 5. By analyzing said pressure trend over time, the control unit establishes if the soft warmer bag 30 is connected to the extracorporeal blood circuit 3, 5 at the heating zone 29. By way of example, the measured pressure trend is compared with a predetermined pressure trend. The way to detect the soft warmer bag 30 connection is identified by using the bag 30 propensity to collapse. If the soft warmer bag 30 is connected, sucking the fluid implies that the soft warmer bag 30 starts to collapse until it works like a closed valve and sucking is prevented or almost prevented. It is not possible for the pump to suck fluid from the warmer bag which collapses as soon as its internal pressure becomes lower than atmospheric pressure. If the warmer bag 30 is not connected, sucking the fluid does not imply the soft warmer bag 30 to collapse. The pressure trend over time in this two situations is different and allows to establish if the soft warmer bag 30 is properly connected or not.

If the soft warmer bag 30 is not properly connected, the control unit may trigger a warning.

Specific examples of the procedure and method are disclosed in the followings passages.

EXAMPLE 1

The return clamp 28 is kept opened (return line 5 opened to atmosphere), the first pinch valve 16 is set in the neutral position and the second pinch valve 21 is set in the post position.

The blood pump 6 is run backwards (counter clock wise) at high flow rate (about 400 ml/min) for some seconds (about 10-15 seconds).

If, during the backwards running of the blood pump, the withdrawal pressure "Pwdr" measured by the withdrawal pressure sensor 25 decreases, or if the difference between the withdrawal pressure "Pwdr" and the return pressure "Pret" decreases, the soft warmer bag 30 is connected (FIG. 1).

Figure 2:
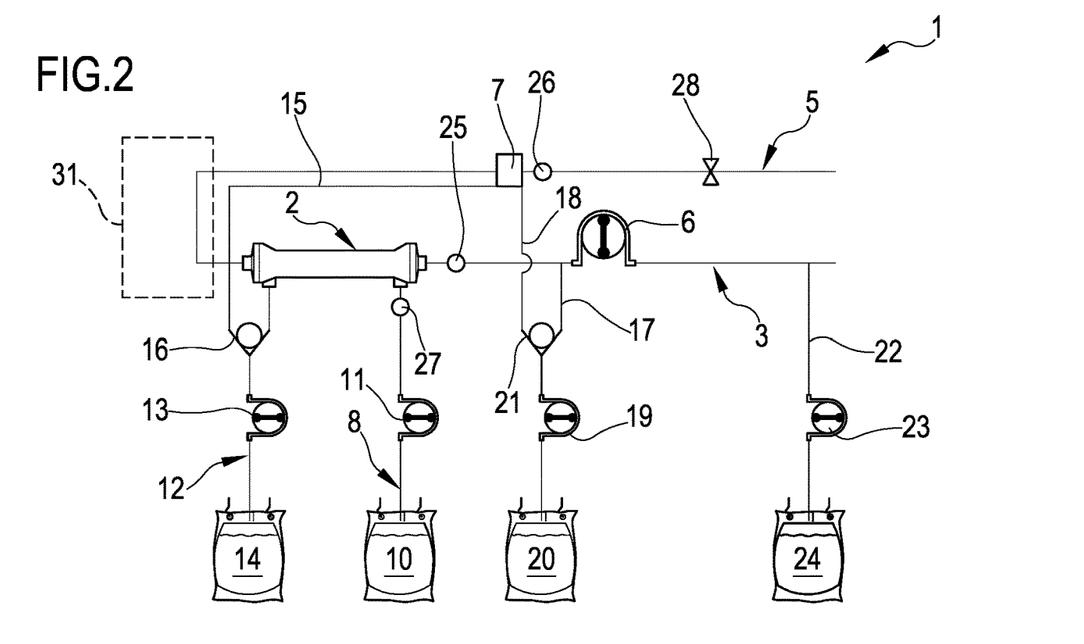
FIG. 2 shows a configuration of the apparatus of FIG. 1 in which the soft warmer bag is not connected.
Figure 5:
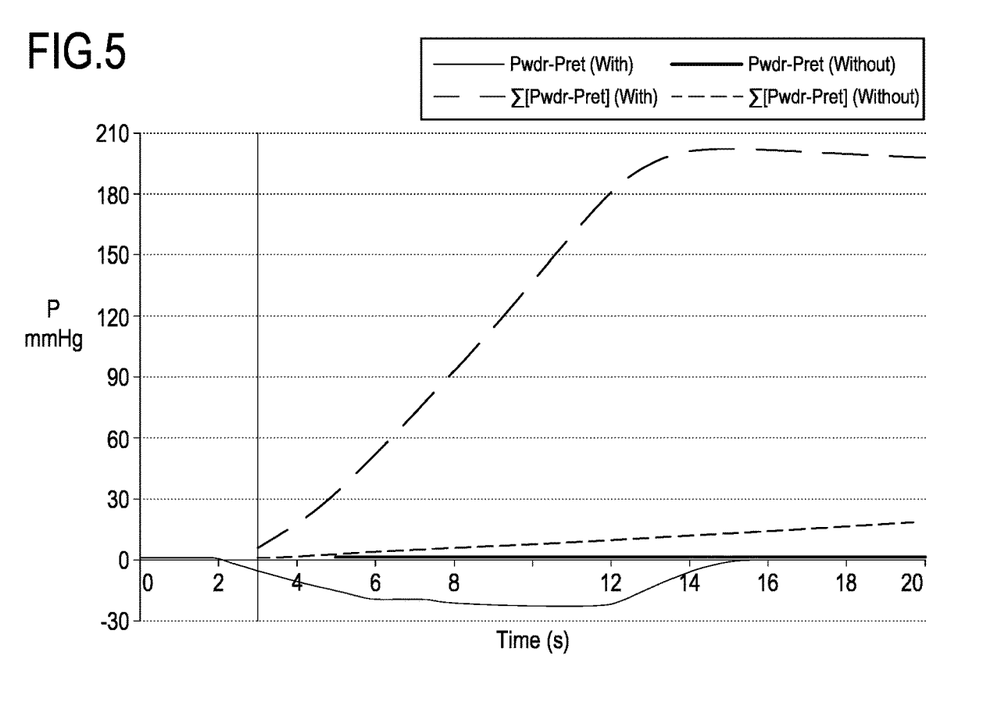
FIG. 5 is a graph showing pressure trends related to an embodiment of the method/procedure of the invention.
Figure 6:
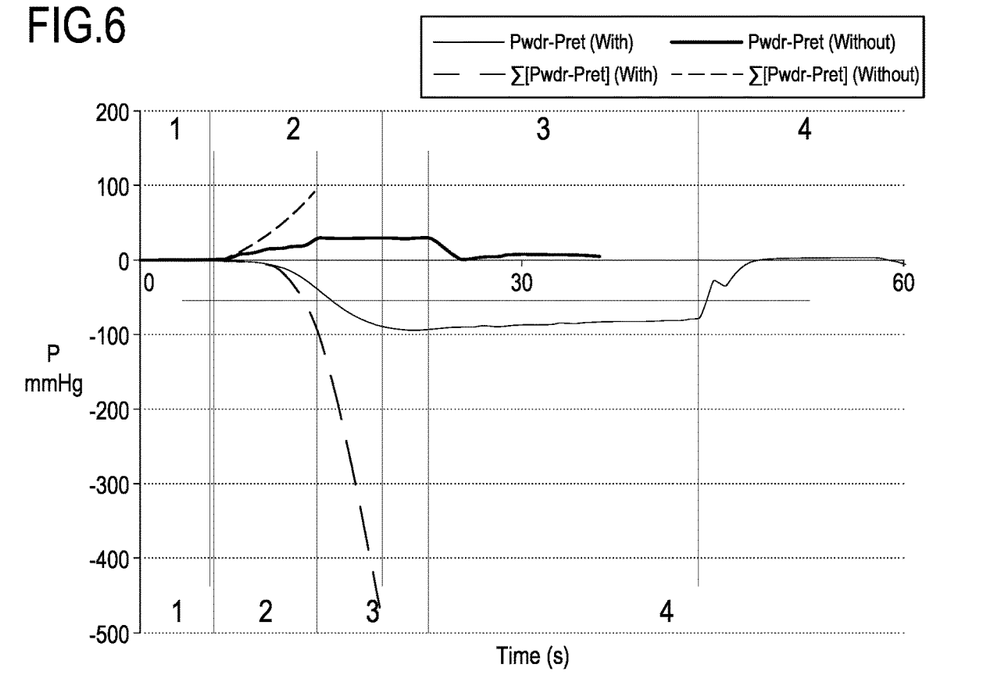
FIG. 6 is a graph showing pressure trends related to the method/procedure of the flowchart of FIG. 4.

FIG. 5 shows that if the withdrawal pressure "Pwdr" measured by the withdrawal pressure sensor 25 stays similar to the return pressure "Pret" measured by the return pressure sensor 26, or if the difference between the withdrawal pressure "Pwdr" and the return pressure "Pret" is zero or close to zero, the soft warmer bag 30 is not connected and the return line 5 goes with no interruption from the blood treatment device 2 to the return clamp 28, like in FIG. 2. This means that the soft warmer bag 30 was not installed at all and the blood return line 5 is a single uninterrupted tube. FIG. 6 shows also the integrated values of the differences "Pwdr-Pret".

EXAMPLE 2

This second example is derived from the previous first example. In this case, the return clamp 28 is kept closed until the end of testing (see Table 1).

The first pinch valve 16 is set in the post position and the second pinch valve 21 is set in the post position too. The blood pump 6 is run backwards (counter clock wise) at high flow rate (about 400 ml/min) for about ten seconds, till the return pressure "Pret" reaches a predefined threshold.

Definitions and Annotations

| | |
|---|---|
| RC | Return clamp |
| LP | Second pinch valve |
| UP | First pinch valve |
| Pwdrx | Withdrawal pressure at phase x |
| Pretx | Return pressure at phase x |
| Ptest | Pressure test target for "Bag detection test" |
| PTbag | Pressure threshold for bag presence |

TABLE 1

Short description of example 2 test sequence

| Phase | LP | UP | RC | Blood pump |
|---|---|---|---|---|
| 1 Set values | Post | Post | Closed | Stopped |
| 2 Air sucking | Post | Post | Closed | 60 rpm backwards |
| 3 Diagnose | Post | Post | Closed | Stopped |

Figure 4:
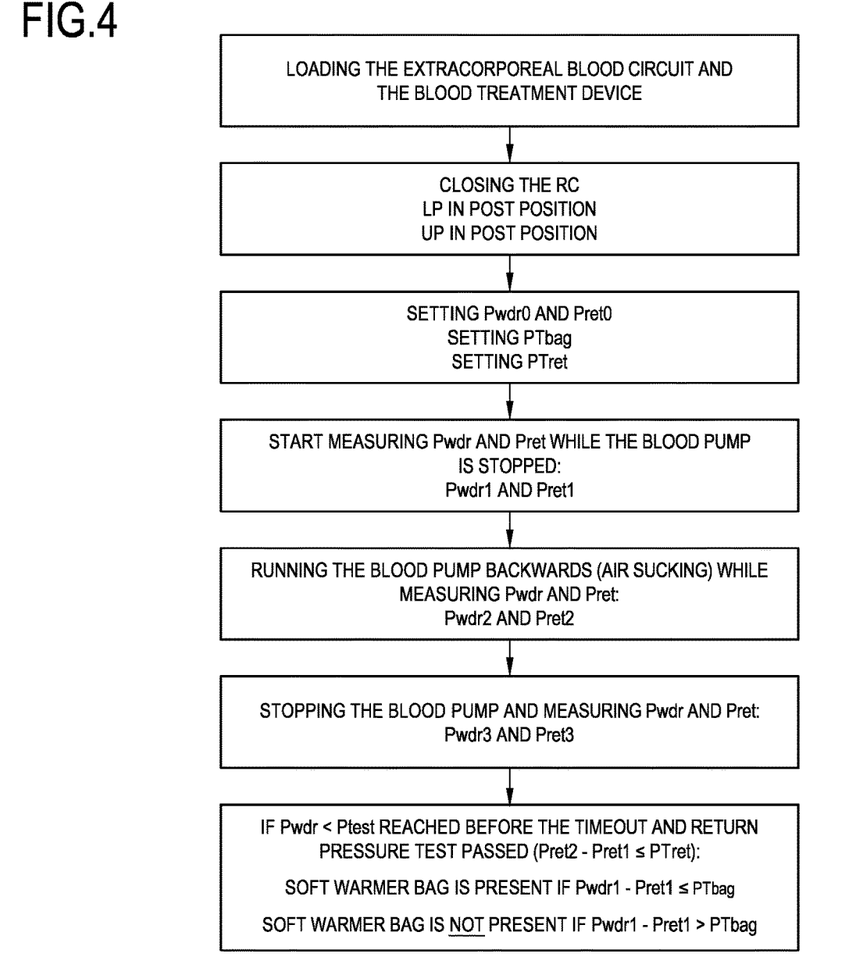
FIG. 4 is a flowchart of one embodiment of a method/procedure of operating the extracorporeal blood treatment apparatus of FIGS. 1 and 2 to detect the soft warmer bag.

FIG. 4 shows a flowchart of the procedure and method of example 2. FIG. 6 shows the trend, during the previous phases 1-4 of table 1, of the difference "Pwdr-Pret" between the withdrawal pressure "Pwdr" and the return pressure "Pret" when the soft warmer bag 30 is connected like in FIG. 1 (continuous thin line) and when the soft warmer bag 30 is not connected (continuous thick line) and the return line 5 is not interrupted but goes from the blood treatment device 2 to the return clamp 28, as shown in FIG. 2. The integrated values of the differences "Pwdr-Pret" are correspondingly plotted in the same figure.

Analysis of withdrawal and return pressure kinetics, in particular during phases 2 and 3, allows diagnosing for the soft warmer bag 30 presence. Phases 2 and 3 last for a time frame "Δt" of about 15 s. During phase 2, blood pump is run till Pwdr reaches a predefined threshold (-80 mmHg as example), with a time limit (which is actually a pumped volume limit).

FIG. 6 illustrates a very significant dependence of "Pwdr-Pret" pressure profile on the presence or not of the soft warmer bag 30 in the circuit. If the soft warmer bag 30 is properly connected, during phases 2 and 3, the difference "Pwdr-Pret" clearly decreases. If the soft warmer bag 30 is not present, during said phases 2 and 3, the difference "Pwdr-Pret" slightly increases.

Please note that the displayed Pwdr pressure in FIG. 6 does not match with the actual circuit pressure but the one sensed by the filter pod (which is not able to measure pressure more negative than about -100 mmHg in the reported example).

Consideration of integrated values rather than steady pressures may make the test more robust.

Additional criteria may be added to check for the validity of pressure values (and proper installation of the lines/sensors).

EXAMPLE 3

In this third example the treatment fluid pump 13 runs backwards instead of the blood pump 6.

The return clamp 28 is kept closed until the end of the testing (see Table 2).

During air sucking and diagnose (see table 2 below) the first pinch valve 16 is set in the post position and the second pinch valve 21 is set in the post position too.

The treatment fluid pump 13 runs backwards (counter clock wise) at high flow rate (about 150 ml/min) for about eight seconds, till the return pressure "Pret" reaches a predefined threshold (PTret).

TABLE 2

Short description of example 3 test sequence

| Phase | LP | UP | RC | Treat. fluid pump |
|---|---|---|---|---|
| 1 Set values | Post | Post | Closed | Stopped |
| 2 Air sucking | Post | Post | Closed | 150 rpm backwards |
| 3 Diagnose | Post | Post | Closed | Stopped |

Figure 7:
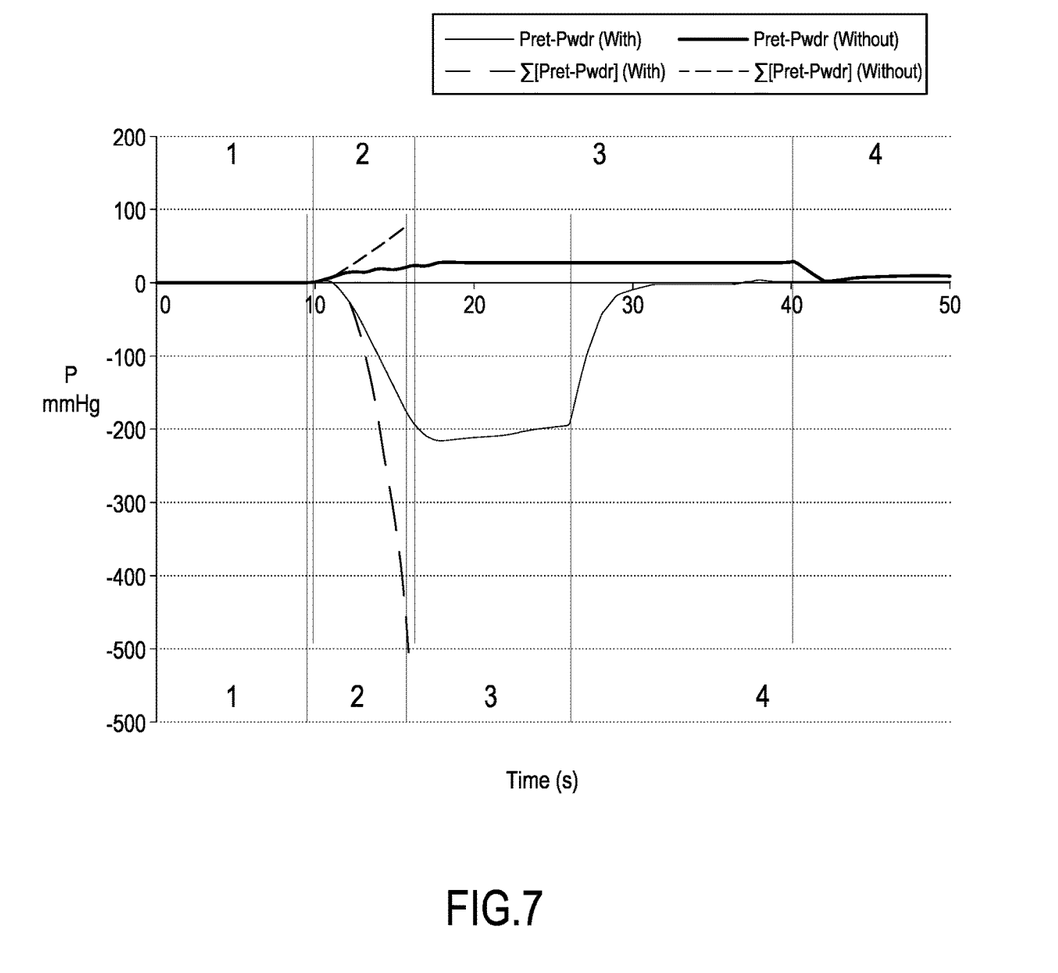
FIG. 7 is a graph showing pressure trends related to another embodiment of the method/procedure of the invention.

FIG. 7 shows the trend, during the previous phases 1-4 of table 2, of the difference "Pret-Pwdr" between the return pressure "Pret" and the withdrawal pressure "Pwdr" when the soft warmer bag 30 is connected like in FIG. 1 (continuous thin line) and when the soft warmer bag 30 is not connected (continuous thick line) and the return line 5 is not interrupted but goes from the blood treatment device 2 to the return clamp 28, as shown in FIG. 2. If the soft warmer bag 30 is not present, during phases 2 and 3, the difference "Pret-Pwdr" slightly increases. If the soft warmer bag 30 is properly connected, during said phases 2 and 3 (time frame "Δt" of about 16 s-17 s), the difference "Pret-Pwdr" clearly decreases. FIG. 7 shows also the integrated value of the differences "Pret-Pwdr".

Analysis of filter, return pressure and evacuation kinetics allows diagnosing for the soft warmer bag 30 presence.

FIG. 7 illustrates a very significant dependence of "Pret-Pwdr" pressure profile on the presence or not of the warmer in the circuit. Consideration of integrated values rather than steady pressures may make the test more robust.

Figure 3:
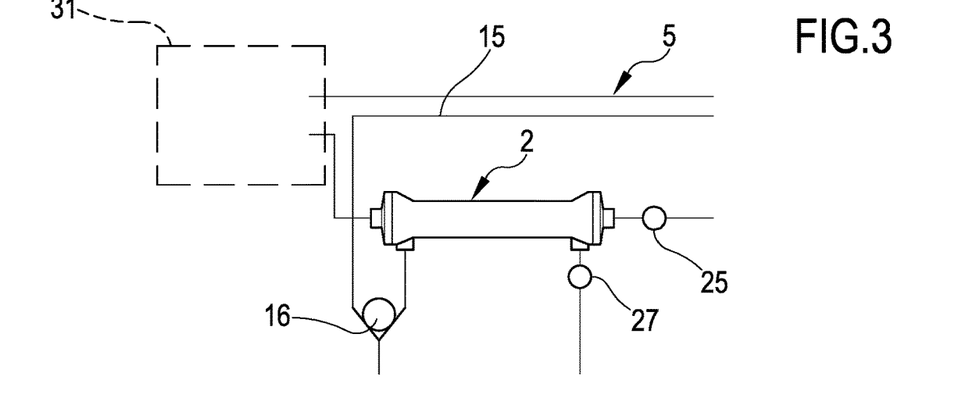
FIG. 3 shows part of the apparatus of FIG. 1 in another configuration in which the soft warmer bag is not connected.

If the soft warmer bag 30 is present but not connected, as shown in the schematic circuit of FIG. 3, the pressure trends without bag ("Pret-Pwdr" or "Pwdr-Pret" or integrated values) are different from those shown in examples 1, 2 and 3. Anyway, said pressure trends without bag are different from the pressure trends with bag and wrong connection or disconnection of the soft warmer bag 30 may be detected the same.

EXAMPLE 4

In this other example, the test is performed after priming and the circuit is closed, sealed from the external environment, and full of priming fluid.

The second pinch valve 21 is set in post position, the first pinch valve 16 is set in neutral position and the return clamp 28 is closed. The blood pump 6 is run backwards at high flow rate (about 400 ml/min) till return pressure reaches a predefined threshold (PTret). After some seconds of stabilization, the return clamp 28 is opened. Analysis of withdrawal and return pressure kinetics allows diagnosing for the soft warmer bag 30 presence.

The present invention may also be used to detect the connection of soft bags other than warmer bags. By way of example and turning again to FIG. 1, the evacuation fluid line 8 is provided with a first pressure sensor 25 placed between the collection bag 10 and the evacuation fluid pump 11. The collection bag 10 is a soft bag connectable to the evacuation fluid line 8 at a connecting zone 29. The first pressure sensor 25 is connected to the control unit 32 and, according to a method similar to the one detailed for the warmer bag 30, may be used to sense a first pressure P1 and to detect the connection of the collection bag 10 to the evacuation fluid line 8 at the connecting zone 29.

Even if FIGS. 1 and 2 do not show any other pressure sensor on the fluid lines (treatment fluid line 12, evacuation fluid line 8, pre-infusion and post-infusion lines 17, 18), a pressure sensor may also be implemented in one or more of the said other fluid lines, by way of example between the respective soft bag (treatment fluid bag 14, infusion fluid bag 20, collection bag 10) and the respective pump (evacuation fluid pump 11, treatment fluid pump 13, infusion fluid pump 19), to detect the connection of the said soft bags.

Figure 8:
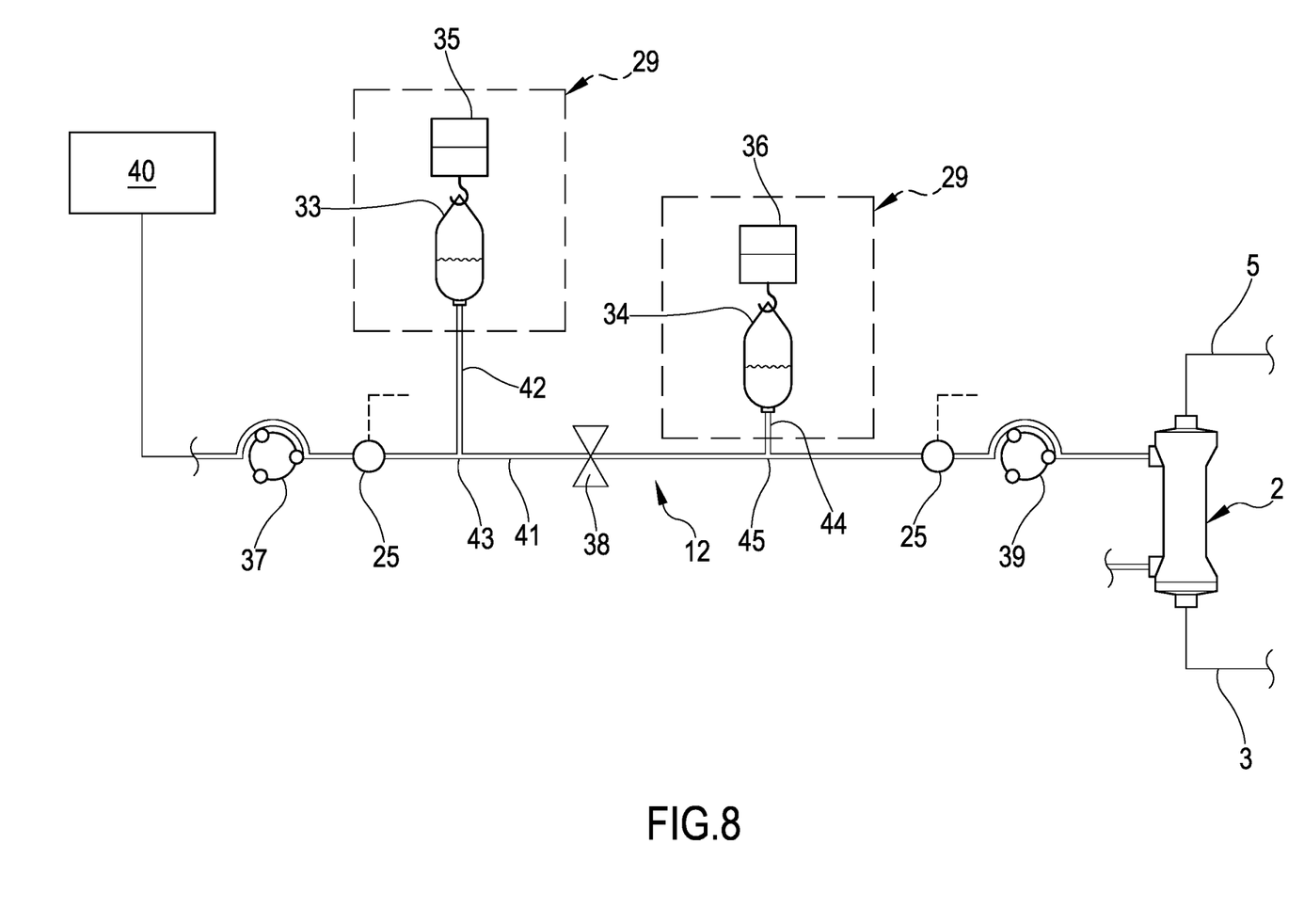
FIG. 8 shows an embodiment of a fluid treatment line of the apparatus of FIG. 1.

FIG. 8 shows another embodiment of the treatment fluid line 12 connected to the blood treatment device 2. The treatment fluid line 12 of FIG. 8 includes components related to the delivery of treatment solution in the blood treatment apparatus 1. Those components include: a first intermediate container 33, a second intermediate container 34, a first gravimetric scale 35, a second gravimetric scale 36, a first fluid pump 37, a valve 38, a second fluid pump 39, a treatment solution source 40.

In the embodiment depicted in FIG. 8, gravity is used to, in part, control the loading and unloading of the first intermediate container 33 and the second intermediate container 34. In particular, the vertical position of the first intermediate container 33 relative to the second intermediate container 34 is used in combination with the valve 38, the second fluid pump 39 and the first fluid pump 37 to selectively load and unload the first and second intermediate containers 33 and 34.

The first fluid pump 37 is connected to the second fluid pump through a first fluid line 41. The first intermediate container 33 is in fluid communication with the first fluid line 41 through a second fluid line 42 which connects to the first fluid line 41 at first junction 43. The second intermediate container 34 is in fluid communication with first fluid line 41 through a third fluid line 41 which connects with the first fluid line 41 at a second junction 45. The valve 38 is, in the depicted embodiment, positioned along the first fluid line 41 between junctions 43 and 45.

The first and second intermediate containers 33, 34 are soft bags connectable to the respective fluid lines 42, 44 at the connecting zones 29. A pressure sensor 25 is placed between the first fluid pump 37 and the first junction 43. A further pressure sensor 25 is placed between the second junction 45 and the second fluid pump 39. The pressure sensors 25 are connected to the control unit 32 (shown only in FIG. 1).

Before starting patient treatment, the connection of the soft bags 33, 34 may be checked by sucking a medium from the connecting zones 29 through the first and/or second fluid pump/s 37, 39 and
measuring at least a pressure trend over time in the first fluid line 41 through the pressure sensor/s 25.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. An extracorporeal blood treatment apparatus comprising:
   a blood treatment device;
   an extracorporeal blood circuit coupled to the blood treatment device;
   a blood pump configured to be coupled to a pump section of the extracorporeal blood circuit;
   a fluid circuit operatively connected to the extracorporeal blood circuit and at least a fluid pump configured to be coupled to the fluid circuit, wherein the extracorporeal blood circuit and/or the fluid circuit present/s a connecting zone configured to be connected to at least a soft bag respectively for blood or for a fluid;
   at least a pressure sensor configured to measure at least a pressure in the extracorporeal blood circuit or in the fluid circuit; and
   a control unit configured to check the connection of the soft bag to the extracorporeal blood circuit or to the fluid circuit through the following procedure:
      (i) sucking a medium from the connecting zone through the blood pump or through the fluid pump,
      (ii) measuring at least a pressure trend over time in the extracorporeal blood circuit or in the fluid circuit through said at least a pressure sensor, and
      (iii) establishing from said measured pressure trend if the soft bag is connected to the extracorporeal blood circuit or to the fluid circuit at the connecting zone.

2. The apparatus of claim 1, wherein a first line of the blood circuit or of the fluid circuit departs from the connecting zone, wherein the at least a pressure sensor is a first pressure sensor placed between the connecting zone and the blood pump or the fluid pump configured to be coupled to said first line, and wherein measuring at least a pressure trend over time comprises: measuring a first pressure in the first line.

3. The apparatus of claim 2, wherein a second line of the blood circuit or of the fluid circuit departs from the connecting zone, wherein a second pressure sensor is placed between the connecting zone and a clamp placed in the second line, and wherein measuring at least a pressure trend over time includes (i) measuring a second pressure in the second line and (ii) calculating a pressure difference between the first pressure and the second pressure.

4. The apparatus of claim 3, wherein the second line is a blood return line of the extracorporeal blood circuit, wherein the second pressure is a return pressure, wherein the connecting zone is a heating zone and the soft bag is a soft warmer bag, and wherein the heating zone is configured to be connected to the soft warmer bag configured to be housed and heated in a blood warming device.

5. The apparatus of claim 4, wherein sucking a medium from a heating zone includes running the blood pump backwards with respect to blood withdrawal from patient during treatment, wherein the measured pressure trend is obtained by subtracting the return pressure from the withdrawal pressure.

6. The apparatus of claim 4, wherein the heating zone is placed in the blood return line between the blood treatment device and a return pressure sensor, wherein a return clamp is placed on the blood return line, wherein the return pressure sensor is placed between the heating zone and the return clamp, and wherein when sucking the fluid from the heating zone, the return clamp is closed or open.

7. The apparatus of claim 2, wherein the first line is a blood withdrawal line of the extracorporeal blood circuit; wherein the first pressure is a withdrawal pressure, wherein the connecting zone is a heating zone and the soft bag is a soft warmer bag, and wherein the heating zone is configured to be connected to the soft warmer bag configured to be housed and heated in a blood warming device.

8. The apparatus of claim 2, wherein the fluid circuit is a treatment fluid circuit or an infusion circuit, wherein the first line is a fluid line and the soft bag is a dispenser bag for a fluid to be dispensed or a collection bag for a waste fluid to be collected.

9. The apparatus of claim 1, wherein establishing from said measured pressure trend if the soft bag is connected includes determining if the measured pressure trend changes or not.

10. The apparatus of claim 9, wherein determining if the measured pressure trend changes or not is performed during sucking or after sucking.

11. The apparatus of claim 9, wherein determining if the measured pressure trend changes or not is performed during a time frame, wherein said time frame is between 5 seconds and 30 seconds.

12. The apparatus of claim 1, wherein the measured pressure trend decreasing indicates that the soft bag is connected, and wherein the measured pressure trend remaining substantially steady or increasing indicates that the soft bag is not connected.

13. The apparatus of claim 1, wherein the measured pressure trend remaining substantially steady or increasing indicates that the soft bag is connected, and wherein the measured pressure trend decreasing indicates that the soft bag is not connected.

14. The apparatus of claim 1, wherein checking the connection of the soft bag to the extracorporeal blood circuit or to the fluid circuit is performed before priming and said medium is air.

15. The apparatus of claim 1, wherein checking the connection of the soft bag to the extracorporeal blood circuit or to the fluid circuit is performed after priming and said medium is priming fluid.

16. The apparatus of claim 1, wherein the control unit compares the pressure trend over time with a reference, before establishing from said measured pressure trend if the soft bag is connected.

17. The apparatus of claim 1, wherein the soft bag is empty or substantially empty from liquids and contains air.

18. An extracorporeal blood treatment apparatus comprising:
   a blood treatment device;
   an extracorporeal blood circuit including a blood withdrawal line and a blood return line coupled to the blood treatment device, wherein the extracorporeal blood circuit presents a heating zone configured to be connected to at least a soft warmer bag configured to be housed and heated in a blood warming device;
   a blood pump configured to be coupled to a pump section of the blood withdrawal line;
   at least a fluid line connected to the extracorporeal blood circuit;
   at least a fluid pump configured to pump fluid through said fluid line;
   at least a pressure sensor configured to measure at least a pressure in the extracorporeal blood circuit; and
   a control unit configured to check the connection of the soft warmer bag to the extracorporeal blood circuit, before starting patient treatment, according to the following procedure:
      (i) sucking a fluid from the heating zone through the blood pump or through the fluid pump or both of them,
      (ii) measuring at least a pressure trend over time in the extracorporeal blood circuit through said at least a pressure sensor, and
      (iii) establishing from said measured pressure trend if the soft warmer bag is connected to the extracorporeal blood circuit at the heating zone.

19. The apparatus of claim 18, wherein the procedure further comprises:
   setting values of a withdrawal pressure in the blood withdrawal line and of a return pressure in the blood return line while the blood pump and the fluid pump are stopped;
   sucking the medium from the heating zone through the blood pump or through the fluid pump while measuring the withdrawal pressure and the return pressure; and
   stopping the blood pump or the fluid pump and keep on measuring the withdrawal pressure and the return pressure.

* * * * *